United States Patent [19]

Oetliker et al.

[11] Patent Number: 4,943,159
[45] Date of Patent: Jul. 24, 1990

[54] METHOD AND APPARATUS FOR GUIDING AND COLLECTING LIGHT IN PHOTOMETRY OR THE LIKE

[75] Inventors: Hans Oetliker, Muri; Peter Winiger, Wohlen; Sonja Stempfel, Zurich, all of Switzerland

[73] Assignee: Inotech AG, Wohlen, Switzerland

[21] Appl. No.: 160,534

[22] Filed: Feb. 26, 1988

Related U.S. Application Data

[63] Continuation-in-part of Ser. No. 919,257, Oct. 15, 1986, which is a continuation of Ser. No. 731,868, May 8, 1985, abandoned, which is a continuation-in-part of Ser. No. 684,482, Dec. 21, 1984, abandoned.

[30] Foreign Application Priority Data

Dec. 24, 1983 [DE] Fed. Rep. of Germany ....... 3347080

[51] Int. Cl.[5] ...................... G01N 21/49; G01N 21/64; G01N 21/59
[52] U.S. Cl. ...................................... 356/73; 356/338; 356/417; 356/440; 250/458.1
[58] Field of Search .................. 356/73, 338, 432, 436, 356/440, 417, 317, 318; 250/458.1, 459.1, 461.1, 461.2

[56] References Cited

U.S. PATENT DOCUMENTS 4,124,302 11/1978 Kuzmin ................................. 356/440

*Primary Examiner*—F. L. Evans

*Attorney, Agent, or Firm*—Bachman & LaPointe

[57] ABSTRACT

A method and an apparatus for guiding and collecting light which arises or is reflected from a sample to be measured is described. The method and apparatus are intended to optimize guiding and collecting the light primarily in fluorimetry, nephelometry, luminometry and the like. The foregoing is achieved by a method which fixes the sample in a first focus of a reflector chamber having an ellipsoidal or paraboidal reflector surface of at least a half ellipsoid of revolution or paraboloid of revolution, and uses beams leaving that material which are reflected by the reflection surface. An apparatus of the kind set forth above is characterized in that at least the material to be measured is surrounded by a reflection surface of at least 2 PI sterradians of ellipsoidal or paraboloidal shape. Detectable light signals are received by a photosensitive surface positioned between a second focus of the reflector chamber and the center of the body of revolution for the case of the ellipsoid. In the case of the paraboloid the light is received after having been reflected at conjugated second and third reflector surfaces by a photosensitive surface orthogonal to the long axis of the reflective body. In another apparatus, the paraboloidal reflector bodies are modified by placing an arc lamp at the focus of the first paraboloid of revolution in order to obtain parallel light of high intensity from a point light source of different wavelengths.

19 Claims, 4 Drawing Sheets

PRIOR ART

METHOD AND APPARATUS FOR GUIDING AND COLLECTING LIGHT IN PHOTOMETRY OR THE LIKE

CROSS REFERENCE TO RELATED APPLICATIONS

This application is a continuation-in-part of U.S. patent application Ser. No. 919,257, filed Oct. 15, 1986 which is a continuation of U.S. patent application Ser. No. 731,868, filed May 8, 1985, now abandoned, which is a continuation-in-part of U.S. patent application Ser. No. 684,482, filed on Dec. 21, 1984, now abandoned.

BACKGROUND OF THE INVENTION

The invention relates to a method and apparatus for guiding and collecting light which issues from a light source and which is passed as an incident primary beam to a specimen or like material to be measured, by which a measuring beam leaving the material to be measured is conducted to at least one detector or the like photoelectric receiver.

When measuring radiation outputs, the signal amplitude of the detector is directly dependent on the intensity of the light to be measured. In that procedure, however, signal noise occurs, produced by the light and the detector, which, because of the random nature of the noise, rises in a sub-proportional fashion relative to the total light detected (the noise increases approximately with $\sqrt{1/J}$). Therefore, because of severe noise, very weak signals or very slight changes in a signal cannot be detected, or can only be detected with difficulty, using expensive technical equipment and long measuring integration times. It is therefore crucial for the light output of the system to be maximized in order to produce a good signal-to-noise ratio.

Very weak signals are produced primarily in the area of luminescence measuring operations. Luminescence phenomena are based on the conversion of absorbed energy into light radiation by suitable molecules. When energy is absorbed, the molecule to be observed jumps to a higher level of oscillation. The excitation energy used is generally a high-energy primary light beam, the wavelength of which differs from that of the measuring beam. Within a period of about 10-12 seconds, the excited molecule gives off a large part of the absorbed energy again by impact with the adjacent molecule. A small part of the absorbed energy can be given off again by the molecule in the form of photons in any direction, and can then be quantified by a measuring means which is capable of selectively detecting the light which is produced in that way. Generally, the degrees of intensity of the primary beam and the measuring beam differ by powers of ten.

Conventional light measuring means detect the measuring light which is irradiated in all directions only within a solid angle of a few degrees (2 to 3 degrees). The remainder of the light remains unused, and can in fact interfere with the measuring operation, in the form of stray or spurious light. Although the measuring arrangement may be of such a configuration, at high technical expense, that so-called single photon counting is made possible, such equipment is however unsuitable for routine measuring operations as it requires long measuring times and is technically exacting.

In luminometry, an increase in the intensity of the primary light does not result in a clear improvement in the measuring operation as only a small fraction of the input energy can be given off again in the form of luminescence. In contrast, high levels of intensity of primary light increase the problems of selectively detecting the secondary or measuring light as the stray or spurious light components are increased at the same time. Likewise, an unsuitable way of improving the measuring operation is to increase the concentration of luminescing molecules, as with an increasing level of concentration, the so-called concentration extinction phenomenon (saturation) becomes more and more noticeable. The more highly concentrated a solution of excited molecules is, the more frequently does an excited molecule lose all its energy by impact against adjacent molecules, before it can emit light. Therefore, it is only in respect of heavily diluted solutions and constant primary light that the level of intensity of a given fluorescence wavelength is proportional to the concentration of the fluorescing substance.

Luminescence measuring operations are primarily used nowadays in the area of clinical research and analysis. However, the methods of investigation are subject to limits by virtue of the inadequate degree of sensitivity of routine measuring equipment, as is required for measuring levels of physiological concentration in the biologically clinical area. Great efforts are being made at this time to replace radioimmunoassays (RIA) which rePresent a health risk from the point of view of the laboratory personnel, by fluorescence immunoassays (FIA). FIAs represent a method which is comparable to RIAs, in regard to its theoretical sensitivity but which has never achieved the expected breakthrough in the laboratory in the absence of suitable routine equipment. The present invention seeks to contribute to improving that situation.

Very weak and in particular imprecise signals also occur in absorption measuring operations in respect of media which have a strong light-scatter of diffusion effect. As conventional photometers only detect the light which passes in a straight line through the specimen or sample to be measured, and the attenuation of such light, it is often impossible to measure the actual light absorption of such media. Stray or scatter light problems occur in absorption measuring operations in respect of colloid-like substances such as photographic emulsions, solutions with macromolecules or polymers, or oily liquids. The present invention seeks to contribute to improving that situation.

When a light source such as an arc lamp is used for illumination purposes, it is usually interposed between a spherical mirror and a lens, the two being arranged in such a way that the arc lamp is in their focal point. This leads to quasi-parallel light which strictly speaking is only parallel for one particular wavelength of light and is disturbed by the spherical aberration of the lens. In addition, only a relatively small solid angle of the light can be used. It is therefore difficult to reach high density light of different wavelengths (or composed light) by focusing the light arising out of such a system afterwards by lenses. An alternative technique which is used is the application of lasers as light sources of high luminous density. This technique suffers the disadvantages of low stability, limited wavelength range and high costs. While it is relatively easy to stabilize the total output of an arc lamp to 1/1000 in relative intensity units, it is not possible to produce strictly parallel light as mentioned above. There is a lack of light source combining high stability, large wavelength range and highly parallel radiation output which is highly desirable for certain applications like microfluorimetry and fluorimetry in general and photo-bleaching or photo-activation in the microscopic range. The present invention allows one to construe a light source fulfilling the above desirable characteristics.

SUMMARY OF THE INVENTION

Having regard to those considerations, the inventor set himself the aim of providing a method and an apparatus of the kind set forth in the opening part of this specification, while avoiding known disadvantages; the method and apparatus are intended to quantitatively optimize the guiding and focussing or collection of light, without a loss in respect of qualitative measuring options.

The object of the present invention is achieved in that the material to be measured is surrounded by a reflection surface covering two PI space angle. The material being of small dimension as compared to the focal length of the reflection surface is disposed at a focal point of a reflection surface which is formed at least as half an ellipsoid of revolution, and beams leaving said material to be measured are reflected at the reflection surface, wherein the primary beam is passed in a straight line therethrough or radiated directly in the center of the material to be measured. When the sample diameter is not negligibly small as compared to the focal length, each combination of sample size and focal length of the ellipsoid must be optimized for maximal light output in terms of deviation of positioning the sample on the long axis of the reflective body for maximal light output integrated over the total volume of the sample. Optimization is preferably carried out by a computer with suitable software and programming.

Another object of the present invention is to provide a radiation collection apparatus for photometric purposes which collects close to 100% of the incident primary beam passed through the specimen fixed at a first focus F1 which allows the measurement of absorption or transmission properties of turbid solutions or material.

A related object of the present invention is in addition to provide a light collecting apparatus for spectral analysis whereby the sample is placed at the focus F1 if its diameter is small as compared to the focal length of a paraboloid and light is collected by means of a combination of reflecting paraboloids of revolution wherein one paraboloid surrounds the material to be measured by at least half a sphere, while the second paraboloid mounted at the optical axis of the first one with its reflecting surface facing the reflection surface of the first one reflects the light being parallel to the optical axis and coming from the first reflection surface through its focus onto a third mirror having a shorter focal length than a second mirror and facing the reflective surface of the second mirror too.

Another related object of the present invention is to provide a radiation collector apparatus for illumination purposes which can be used to collect and parallelize light from an illumination source such as a short arc lamp positioned in the focus of a primary paraboloid for high intensity, high stability and small diameter illumination.

The invention, further important details and features of which are to be found in the claims, is in principle based on the consideration that the incident measuring beam of the intensity $I_o$ can be brought into the focal point of a reflective ellipsoid, or forms which are approximate thereto, by means of light conductors or guides or optical focussing methods, and there passes through the material to be measured. The detector or a suitable member for collecting light is disposed at another focal point of the ellipsoid of revolution where virtually 100% of the light which issues from the specimen or sample again can be collected. This gives a major improvement in comparison with conventional light guide means as long as the aim is to detect the secondary radiation from the sample or specimen in as quantitative fashion as possible.

The invention relates primarily to all photometric means which measure luminescence phenomena, such as for example phosphorescence, fluorescence, liquid scintillation counting wherein the measuring means makes it possible to simultaneously provide for fluorescence emissions with very high output, diffusion and absorption of the excitation light and spectral analysis of the emitted fluorescence light.

The most efficient and at the same time simplest improvement in measurement in the area of luminometry can only be achieved by an improved light guide and collection system. For that purpose, the invention has three improvements over conventional luminometers:

(a) due to the rotational-elliptical or paraboloidal light collecting system, the light output of the measuring light is improved by a factor of 50 to 100;

(b) by virtue of the possibility of radiating the primary light directly in the center of the material to be measured, a marked reduction in inherent absorption of the excitation energy is achieved; and (c) due to the reflection paraboloids for the first time conventional qualitative measuring options are combined with optimum quantitative light output.

A further use of the present invention is in the construction of a lens free lamp system with high luminous density and high parallelity and output stability for microfluorimetry and the like. Such lamps have the unique advantage that the focal points for UV radiation are not different from the ones of visible light therefore facilitating greatly the adjustment of the lamp in UV-applications.

Figures 6, 7, 8:
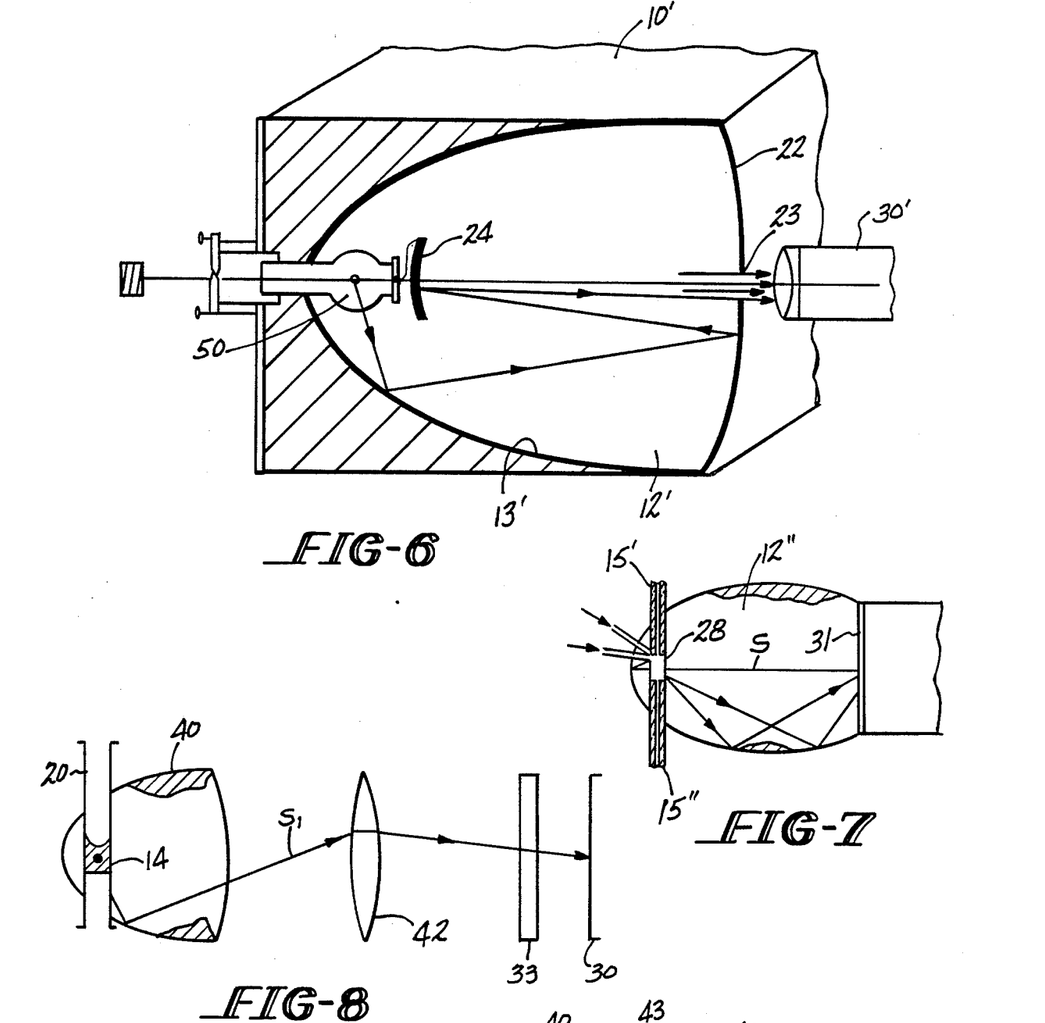
FIG. 6 shows the use of a paraboidal mirror for illumination purposes.
FIGS. 7 through 14 show different forms of a test tube or container and different arrangements for light guiding which can be used with the measuring units of the present invention.

A still further use of the invention lies in nephelometric analysis. As is well known nephelometric analysis is a method of quantitative analysis of solutions of turbid substances by means of measurement in respect of the intensity of the scatter light (tyndallimetry) or by means of measurement of apparent extinction (turbidimetric analysis). For the purpose of nephelometric analysis, the present invention is modified as shown in FIG. 7 in the following fashion: the incident measuring beam is passed in a straight line (90° with respect to the longitudinal axis) through the ellipsoid of revolution, only interrupted at the focus by the specimen or sample chamber. The light which is not scattered or diffused by the sample or specimen is measured in a straight line opposite the point of entry, while the diffused light is measured by means of a detector at the second focus of the ellipsoid of revolution.

The present invention makes it possible for the first time for both measurements to be performed simultaneously as a routine step, in order to check off the values in comparison with each other. In the area of scatter light measurement moreover, a marked improvement in the measuring operation is achieved by virtue of detecting all the scatter or stray light. In that way, it is possible to better measure slight scatter phenomena or changes in scatter factor of solid, liquid or gaseous substances and mixtures thereof or transitional forms such as for example emulsions, variations in scatter factor of cell structures or components thereof in culture solutions or the variations in scatter factor in the growth of bacteria and yeasts.

The present invention can also be used for photochemical applications. It is known that many chemical reactions can be triggered off by light. In that connection, the molecules of the reacting substance must absorb one or more photons, under defined conditions. In the present case, the light is radiated at the one focus of the ellipsoid of rotation by means of light guides or by introducing a lamp. At an oppositely disposed focus, the material to be measured or the reaction material is exposed, in a defined amount, to irradiation on all sides, by means of a static arrangement or dynamically by means of flow cells, for a defined period of time.

The invention therefore provides a novel light guide means for use throughout the photometry art, that is to say for example for:

(a) fluorescence measuring operations;
(b) diffraction measuring operations and nephelometric analysis;
(c) absorption measuring operations;
(d) any luminescence measuring operations;
(e) kinetic measuring operations in use as in (a) to (d);
(f) liquid scintillation counting;
(g) photochemical processes; and
(h) optimized light sources.

The light, modulated or unmodulated, is introduced directly into the interior of the material to be measured, for example by:

- simple, multiple, modified light guides,
- • lens focussing,
- • • mirror focussing.

The light collecting system according to the invention in photometry uses provides that, after passing through the material to be measured, the light is completely or partially collected, making use of virtually the full solid angle (approximately 4), the collecting system surrounding the specimen or sample in three dimensions, in the form for example of:

(1) an ellipsoid of revolution;
(2) a paraboloid of revolution:
(3) a light guide cone;

in approximate or partial configuration.

The invention also provides novel detectors for elliptical light collecting systems, which, in spherical, cubic or approximately or partially spherical or cubic form, are disposed at the focus of the possibly half ellipsoid of revolution. At that focus, for certain situations of use, it is possible to employ a light collecting member as referred to above, with light guide connected thereto, leading to the detector.

Further features, advantages and details of the invention will be apparent from the following description of preferred embodiments and with reference to the accompanying drawings which are basic diagrammatic views. In the drawings:

DETAILED DESCRIPTION

Figure 1:
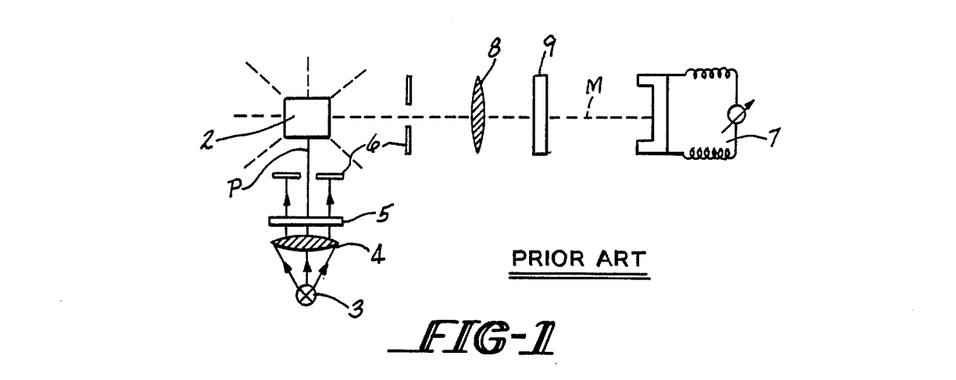
FIG. 1 shows a conventional fluorimeter.

In the diagrammatic view of a fluorimeter 1 as shown in FIG. 1, a sample of specimen test tube or container 2 is disposed at the point of intersection of two axes P and M which extends from a light source 3, being the so-called primary beam. Disposed between the light source 3 and the sample test tube 2 are a lens 4 and a filter 5. Aperture members 6 are located on both sides of the primary beam p. The other axis which is formed by a measuring beam M terminates in a photo-electric cell 7 which also has, disposed upstream thereof, a lens 8 and a filter 9 with associated aperture members 6 disposed beside the beam.

The conventional arrangement shown in FIG. 1 is used for measuring fluorescence, which is generally interpreted as meaning fluorescence spectroscopy as a quantitative method and spectrofluorimetry as a qualitative method.

Figure 2:
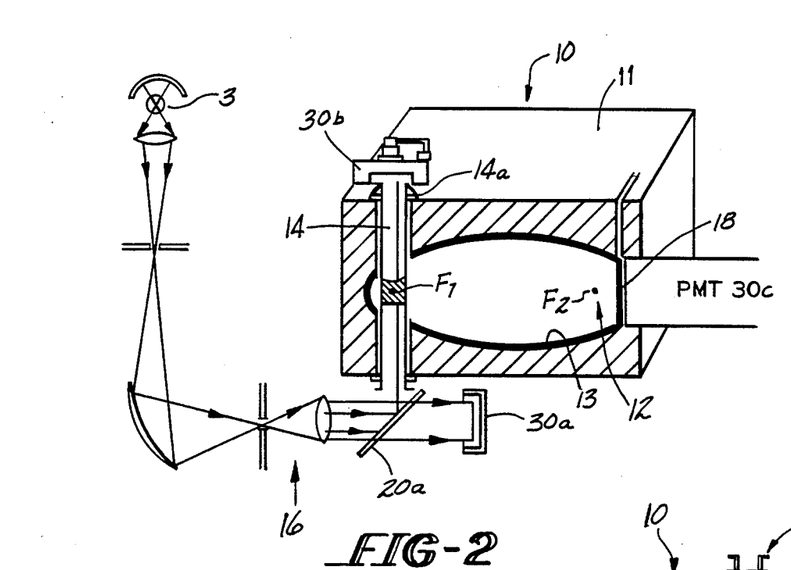
FIG. 2 shows a perspective view of a fluorescence measuring apparatus according to the invention, having a measuring chamber containing a light guiding specimen container and a detector.

FIG. 2 shows a configuration in accordance with the invention of a first embodiment of a measuring block or unit 10 for fluorescence measuring operations. Disposed in the housing 11 thereof is a measuring chamber 12 having a reflection surface, as indicated at 13, in the form of an ellipsoid of revolution. The ellipsoidal reflector surface has the form of an ellipsoid of revolution about a major axis, which is also known as a spheroid. The major axis which is the longitudinal axis forms an axis of symmetry. As with all ellipsoids, the ellipsoidal reflector surface 13 has a first focus F1 and a second focus F2 preferably along the axis of symmetry. By virtue of this geometry, light emanating from the first focus F1 is reflected towards the second focus F2 as illustrated in FIG. 2. In a preferred embodiment, the sample container or compartment 14 consists of a cylindrical tube with a transparent bottom at half of its length, extending parallel to the short axis from one side to the other enclosing focus F1 in its lumen. It is held in place by a cylindrical ring 14a attached to it resting on the reflective body on its outside. The container is positioned so that the sample or specimen is disposed substantially at the first focus F1. Preferably the center of the container is along the axis of symmetry. In addition, the body surrounds the container to an extent close to 2 PI sterradians. The reflector body contains particle free air but could be filled with particle free and degassed fluid if matching of the refractive indices of the walls of the sample compartment and the interior of the reflective body is desirable. The light intensity can be measured in three places by detectors 30a, 30b, 30c. Whereas detector 30a measures a fraction of the light incident to the sample, passing through a semitransparent mirror 20a, allowing one to monitor lamp intensity, detector 30b yields a signal relating to transparency (transmission) of the sample. Detector 30c detects luminescence of the sample or scattered light by the sample.

Figure 3:
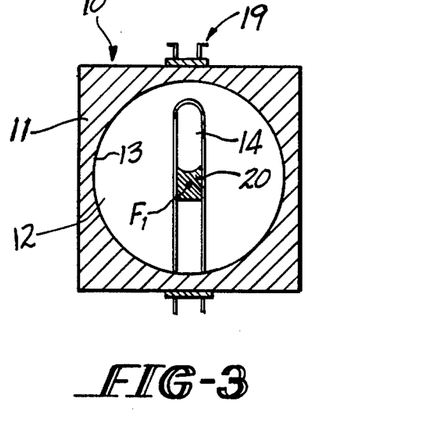
FIG. 3 shows a view in cross-section through the measuring unit approximately along line III—III in FIG. 4.
Figure 4:
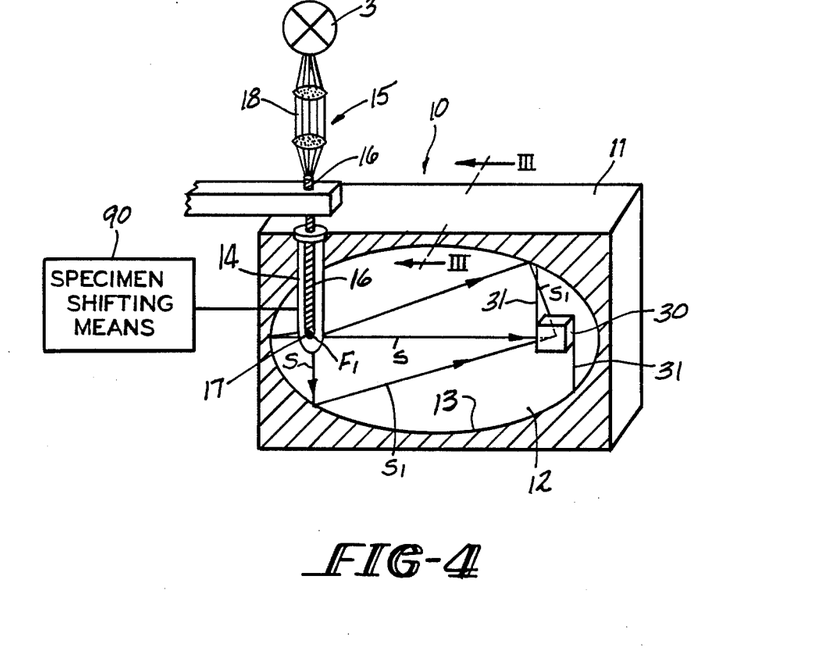
FIG. 4 shows a view in longitudinal section through another embodiment of a measuring unit having an ellipsoid of revolution; a measuring chamber containing a light guide in the test tube and a cubic detector.

As shown in FIGS. 3 and 4, the measuring unit 10 may also include a light conducting device 15 for conducting light from a source to the compartment 14. The light conducting device may be a single light conductor or a multiple light conductor. In addition, the light conducting device 15 may have a lens focussing system 16 associated therewith. A scatter cone 17 for scattering light as shown in FIG. 4 may be disposed at the end of the light conductor which may in turn be located at the first focus F1. Within the measuring chamber, the specimen container 14 which may be a test tube surrounds the light conducting device and the scatter cone 17.

The measuring unit may further include a photo sensitive detector 30 such as a cubic detector oriented at about 90° with respect to the axis of symmetry to receive the measuring beams. As shown in FIG. 4, the measuring beams may pass directly to the detector 30 or be reflected off the reflective surface 13. If desired, a filter 18 may be provided to filter the measuring beams. In a preferred embodiment, the detector 30 is located at the second focus. Alternatively the detector 30 may be positioned intermediate the first and second foci. For certain areas of use, the detector 30 may be provided with a layer or coating 31 which is partially selectively transmissive in respect of light.

In operation, the unit 10 analyzes a specimen by illuminating it with light introduced from a source 3 through a hole 19 in the measuring unit housing 11 and/or light conducting device 15. The light may be passed through a lens and filter system 16 before being directed to the hole by a mirror 20. The light is preferably introduced into the compartment 14 in a way that its direct path does not intersect the reflective body and the primary light beam passes directly into the center of the specimen. This causes at least two kinds of measuring beams to be created. As previously discussed, the beams reach the detector either directly or by reflection off the surface 13. The measuring beam may be a light beam or some other form of radiation emitted by the specimen itself as a consequence of chemical or physical processes going on in the compartment. The foregoing method may be used to analyze processes in living cells or detecting small amounts of chemicals as indicators of processes to be observed such as changes in calcium concentration, pH, redox potential and the like.

Since the size of the specimen and the compartment may vary, means 90 for shifting the specimen compartment depending upon the size of the compartment needed to hold the specimen may be provided. The shifting means may comprise any suitable means known in the art. Preferably the shifting means includes a suitably programmed computer. By shifting the container, one can collect the maximal radiation from a source such as the specimen which has a finite diameter which is not negligibly small as compared to the focal length of the ellipsoidal surface of the reflector body.

Figure 5:
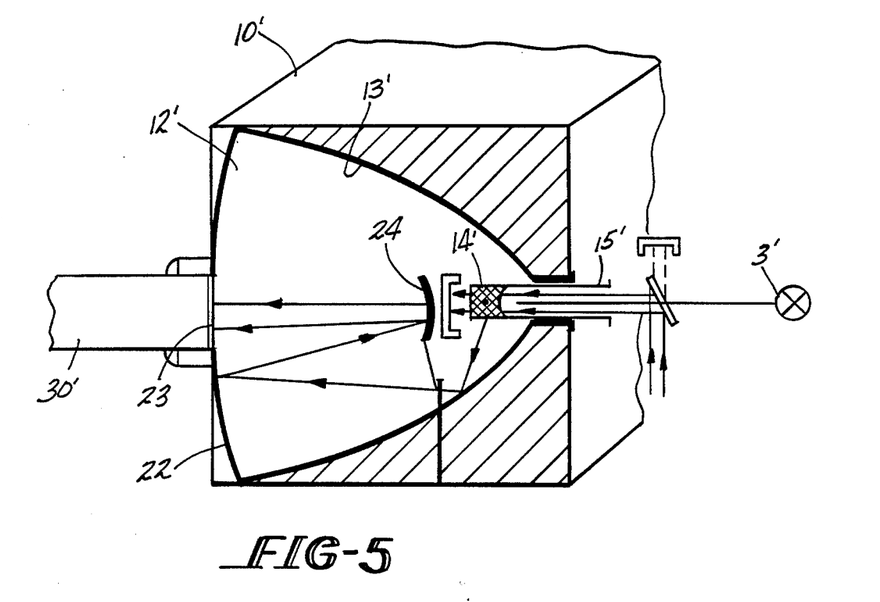
FIG. 5 shows a measuring unit having a cuvette and paraboidal mirrors.

Referring now to FIG. 5, a measuring unit 10' having a chamber 12' defined by a reflector body having a reflective surface 13' with a substantially paraboloidal shape is illustrated. The body is preferably designed so that its axis of symmetry intersects a first focus F1. The chamber is further defined by a second reflector body 22 having a hole 23 at its vertex and a third reflector body 24 intermediate said first focus and the second body. The reflective surface of each of the bodies are substantially concave.

The second reflector body 22 is arranged so that its focal point is located on the optical axis of the first body and has an axis of symmetry coincidental with the axis of symmetry of the first body. The third body 24 is arranged so its concave surface faces the concave surface of the second body 22 and has a focal point arranged relative to the focal point of the second reflector body so that there is an optimization of parallelity for light issuing from the sample from points in space not coincident with the focal point of the first paraboidal surface and the amount of light or detectable radiation, if measuring radiation values, reaching the detector 30' which is positioned behind the hole 23.

As before the specimen to be analyzed lies within a compartment 14' in the measuring chamber 12'. The specimen is illuminated by passing light from a source 3' through a light conductor 15' to the container. The measuring beams reflect off the surface 13' of the first body, pass to the reflective surface of the second body 22, then to the reflective surface of the third body 24 and finally through the hole 23 to the detector 30'. In this regard, the second and third bodies serve to narrow and parallelize the reflected measuring beam. This serves to adapt the radioation to the size of the available photodetector and to allow spectral analysis off a monochromator which can be done only with parallel light.

FIG. 6 shows the use of paraboloidal mirrors for illumination purposes. In this embodiment, an arc lamp 50 is positioned in a reflectorbody as described for FIG. 5 instead of the specimen in such a way within the first refective Paraboloid that the center of the arc coincides with the point F1. Light emitted by the lamps is parallelized and narrowed as described for light arising from the speciment in FIG. 5 leaving the hole 23. This yields a light source supplying highly parallel light output having high stability, large wavelength range and high energy efficiency. Such light sources are required for microfluorimetry. In that connection a molecule capable of emitting fluorescent light in a microscopic preparation has to be excited by an incident primary beam of stable intensity and clearly defined size. High stability or the incident exciting light is of utmost importance for the measurement of fast dynamic changes of fluorescence in restricted compartments of living cells for example. That application is applicable to measurements in fluorimetry in general as well as to foto bleaching or foto activation in the microscopic range.

The measuring chamber 12" shown in FIG. 7 can be used for measuring scattered and unscattered light components from a sample or specimen (nephelometric analysis). A short cylindrical cube-like normal test tube with bottom and top parallel or container 28 is disposed between two light conductors 15' and 15", with the light being passed in a straight line through the sample or specimen to be measured.

In FIG. 8, a convergent lens 42 is disposed downstream of the half ellipsoid of revolution 40, in the beam path S1.

Figure 9:
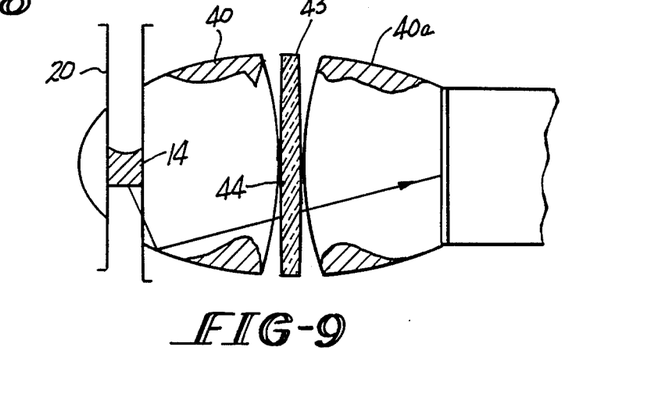

The embodiment shown in FIG. 9 comprises two half ellipsoids of revolution 40 and 40a which are disposed in coaxial relationship with each other and between which a gap 43 provides an opening for inserting filters or the like, as indicated at 44 to block exciting light from reaching the detector which measures fluorescence light.

Figure 10:
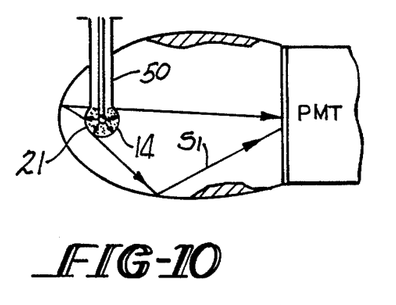
Figure 11:
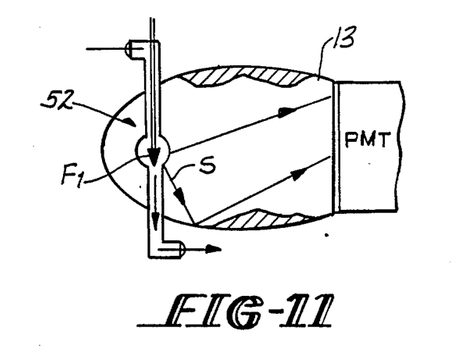

FIG. 10 shows a test tube 50a for measuring the absorption of light, with a spherical end portion 21. Depending on transparency of the sample different amounts of light will reach the PMT, whereby all light not absorbed by the sample will reach PMT (true absorption). FIG. 11 shows a through-flow test tube 52 for the same purpose.

Figure 12:
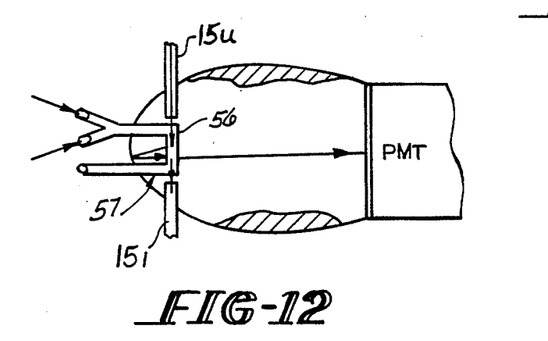

The central portion 56 of a U-shaped test tube 57 as shown in FIG. 12, being what is referred to as a 'STOP AND FLOW' test tube, for measuring kinetic phenomena, as known for those informed in the art, is disposed coaxially between an upper light conductor 15u and a lower light conductor 15l which provide for guiding the light in a straight line and which permit a component of the light to issue through the lower light conductor 15l. The light efficiency of light collection allows one to measure fast reaction with high time resolution.

Figure 13:
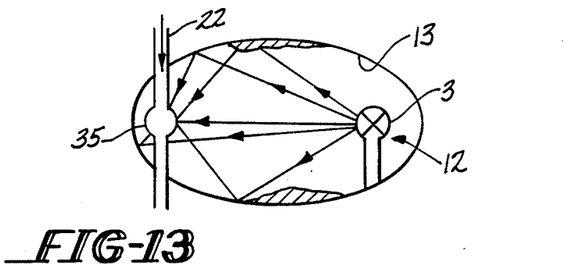

For the purposes of photoactivation of chemical processes, in FIG. 13, the light source 3 is disposed at a focus of an ellipsoid body of revolution. Disposed at the other focus is a reaction cell 35 such as a flow through cell. In this case, the reaction material to be fotoactivated is continuously passed through the one focus by the driving force of a pump, where it is exposed on all sides to defined illumination for a defined period of time.

Figure 14:
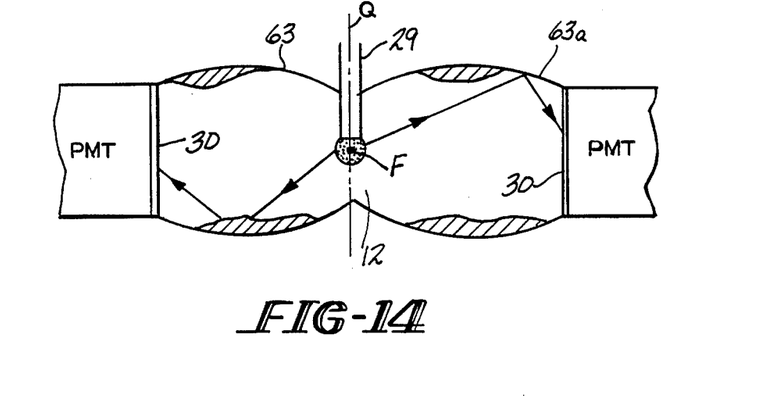

Two ellipsoids of revolution 63 and 63a as shown in FIG. 14, which penetrate each other along a plane or line Q passing through a respective focus F have, as a joint measuring chamber, two detectors 30 and a well known liquid scintillation vial 29 at the joint focus F. That apparatus can be used to measure light flashes in liquid scintillation counting of low-energy radio isotopes. The symmetrical arrangement of the light collecting means makes it possible for light signals which are not radioactively generated to be very substantially cut out, by means of coincidence connection.

It is apparent that there has been provided in accordance with this invention, a method and apparatus for guiding and collecting light in photometry or the like which fully satisfies the objects, means, and advantages set forth hereinbefore. While the invention has been described in combination with specific embodiments thereof, it is evident that many alternatives, modifications, and variations will be apparent to those skilled in the art in light of the foregoing description. Accordingly, it is intended to encompass all such alternatives, modifications, and variations as fall within the spirit and broad scope of the appended claims.

What is claimed is:

1. A method for guiding and collecting light which issues from a light source and which is passed as an incident primary modulated or unmodulated beam to a specimen or like material to be measured comprising:
   providing a measuring chamber defined by a first reflector body having a reflective surface of a desired shape and a longitudinal axis which defines a first axis of symmetry;
   positioning a compartment containing said specimen within said chamber so that said specimen is disposed substantially at a first focus of the reflector body;
   passing a primary light beam from said source through said compartment without said beam being reflected off said reflector body to generate at least two measuring beams; and
   conducting said beams to at least one detector oriented at about 90° with respect to said axis with at least one of said beams being reflected at said reflective surface.

2. A method according to claim 1 wherein said chamber providing step comprises providing a reflector body having a reflector surface with a substantially ellipsoidal shape and surrounding said compartment to an extent close to 2 PI sterradians.

3. A method according to claim 2 further comprising shifting said position of the specimen compartment from said first focus depending on the size of the compartment so as to permit collection of maximal radiation from a source such as said specimen which has a finite diameter which is not negligibly small compared to the focal length of said reflector body with said ellipsoidally shaped reflector surface.

4. A method according to claim 2 further comprising positioning said at least one detector at a second focal point of said body.

5. A method according to claim 1 wherein said chamber providing step comprises providing a first reflector body having a reflector surface with a substantially paraboloidal shape and an axis of symmetry intersecting the first focus, a second paraboloidal reflector body having a central hole at its vertex facing said first body, said second reflector body being arranged so that its focal point is located on an optical axis of the first reflector body and an axis of symmetry coinciding with the axis of symmetry of the first reflector body, a third reflective body disposed between said first focus and said second body and having a concave reflecting surface facing the reflective surface of said second body and a focal point arranged relative to the focal point of the second reflector so that there is an optimization of parallelity and amount of any detectable radiation reaching said at least one detector, and said conducting step comprises reflecting said detectable radiation from said first reflector body to said second reflector body to said third reflector body and through said hole prior to it reaching said at least one detector.

6. A method as set forth in claim 1 wherein said passing step includes radiating a primary light beam directly in the center of the specimen and passing said beams leaving the specimen to a second focus of the reflection surface which is formed as an ellipsoid of revolution.

7. A method as set forth in claim 1 characterized in that, for quantitative analysis of solutions by measuring the intensity of scatter light, said passing step comprises passing the primary beam in a straight line to the specimen through said reflective surface which comprises an ellipsoid of revolution using a light guide tube and interrupting the primary beam with the specimen at the focus and reflecting scattered light from said specimen to a second focus wherein light which is not scattered is measured opposite the entry of the primary beam and scattered light is measured at a second focus of the ellipsoid of revolution surface.

8. A method as set forth in claim 1 including measuring said light beams with a cubic detector.

9. A method for guiding and collecting light which issues from a light source and which is passed as an incident primary modulated or unmodulated beam to a specimen or like material to be measured comprising:
   providing a measuring chamber defined by a first reflector body having a reflective surface of a desired shape and a longitudinal axis which defines a first axis of symmetry;

positioning a compartment containing said specimen within said chamber so that said specimen is disposed substantially at a first focus of the reflector body;

said positioning step including disposing the specimen in a defined amount at said first focus;

passing a primary light beam from said source through said compartment to generate at least two measuring beams;

conducting said beams to at least one detector oriented at about 90° with respect to said axis with at least one of said beams being reflected at said reflective surface; and said light beam passing step comprising emitting light at a second focus of the said body which comprises an ellipsoid of revolution and irradiating the specimen on all sides for a defined period of time.

10. An apparatus for guiding and collecting light which issues from a light source and which is passed as an incident primary beam to a specimen or like material to be measured comprising:

a measuring chamber defined by a first reflector body having a reflective surface of a desired shape and longitudinal axis which defined a first axis of symmetry;

a compartment for holding said specimen positioned within said chamber so that the center of the compartment is along said axis and said specimen is disposed substantially at a first focus of said body;

means for passing said primary beam from said source through said compartment without said beam being reflected off said reflective surface source through said compartment to generate at least two measuring beams; and at least one photo-sensitive detector oriented at about 90° with respect to said axis to receive said measuring beams with at least one of the measuring beams being reflected off said reflective surface.

11. Apparatus as set forth in claim 10 wherein said apparatus comprises a radiation collector device for analyzing low level radiation from said specimen which comprises a small volume sample containing at least one of suspended cell liquid, fluid alone and gas arising from at least one of endogenous light emission of a compound and illumination exciting fluorescence of at least one of the specimen and a chemical compound associated therewith.

12. Apparatus as set forth in claim 10 wherein said reflective surface surrounds said compartment to an extent close to 2 PI sterradians and has a substantially ellipsoidal shape and which further comprises means for shifting said specimen compartment depending upon the size of the compartment needed to hold said specimen in order to collect maximal radiation from a source such as said specimen having a finite diameter which is not negligibly small as compared to the focal length of the ellipsoidal surface.

13. Apparatus as set forth in claim 10 wherein said reflector surface surrounds the compartment to an extent above 1 PI sterradian, has a substantially paraboloidal shape and has its axis of symmetry intersecting said first focus and said chamber is further defined by a second paraboloidal reflector having a central hole at its vertex facing said first reflecting body and a third reflector body having a reflective surface intermediate said first and second bodies, said second body being arranged so that its focal point is located on the optical axis of said first body and has an axis of symmetry coinciding with said first axis, said first and second reflectors further being arranged so concave portions of each reflective surface face each other, said third body further being characterized by a concave surface facing the surface of the second body and a focal point which lies on said first axis and which is arranged relative to the focal point of said second reflector body so as to optimize the parallelity and amount of detectable radiation reaching said at least one detector, and said at least one detector being positioned behind said hole so that said radiation is reflected from said first reflective surface to said second reflective surface, from said second reflective surface to said third reflective surface, and passes through said hole prior to reaching said at least one detector.

14. Apparatus as set forth in claim 10 wherein said at least one detector comprises a cubic detector and said specimen and each said cubic detector are disposed in a body comprising an ellipsoid of revolution at the respective foci thereof.

15. Apparatus as set forth in claim 10 wherein said specimen and a detector are disposed in a measuring chamber comprising a first half ellipsoid forming said first body revolution and a lens convergent system is located downstream of said first half ellipsoid.

16. Apparatus as set forth in claim 10 characterized in that said chamber has a second focus and a gap for accommodating at least one filter and further characterized by said compartment being a test tube which projects into said chamber.

17. Apparatus as set forth in claim 16 wherein the test tube has at least one of a spherical receiving portion at one of said foci and a through-flow test tube construction.

18. Apparatus as set forth in claim 10 characterized in that each said detector is provided with a layer which is selectively light-transmissive.

19. Apparatus as set forth in claim 10 further including light conduction means secured to a holding means outside said measuring chamber and to the source.

* * * * *

UNITED STATES PATENT AND TRADEMARK OFFICE
CERTIFICATE OF CORRECTION

PATENT NO. : 4,943,159

DATED : JULY 24, 1990

INVENTOR(S) : HANS OETLIKER ET AL.

It is certified that error appears in the above-identified patent and that said Letters Patent is hereby corrected as shown below:

IN COLUMN 9, CLAIM 1, LINE 56, AFTER "SPECIMEN" DELETE "OR" AND INSERT --OF--.

Signed and Sealed this

Thirty-first Day of March, 1992

Attest:

HARRY F. MANBECK, JR.

Attesting Officer     Commissioner of Patents and Trademarks